United States Patent
Desjonqueres (10) Patent No.: US 9,144,612 B2
(45) Date of Patent: Sep. 29, 2015

(54) DERMATOLOGICAL COMPOSITIONS CONTAINING AN ASSOCIATION OF PEROXIDE LIPIDS AND ZINC, AND USES THEREOF IN PARTICULAR IN THE TREATMENT OF LABIAL AND/OR GENITAL HERPES

(75) Inventor: Stephane Desjonqueres, Maisons-Laffitte (FR)

(73) Assignee: LABORATOIRES CARILENE, Montesson Cedex (FR)

( * ) Notice: Subject to any disclaimer, the term of this patent is extended or adjusted under 35 U.S.C. 154(b) by 436 days.

(21) Appl. No.: 12/971,055

(22) Filed: Dec. 17, 2010

(65) Prior Publication Data

US 2011/0159106 A1 Jun. 30, 2011

(30) Foreign Application Priority Data

Dec. 24, 2009 (FR) ...................................... 09 59604

(51) Int. Cl.
- *A61K 9/00* (2006.01)
- *A61K 31/327* (2006.01)
- *A61K 33/30* (2006.01)
- *A61K 47/02* (2006.01)
- *A61P 31/22* (2006.01)
- *A61K 47/44* (2006.01)
- *A61K 31/25* (2006.01)
- *A61K 45/06* (2006.01)

(52) U.S. Cl.
CPC ............... *A61K 47/44* (2013.01); *A61K 9/0014* (2013.01); *A61K 9/0034* (2013.01); *A61K 31/25* (2013.01); *A61K 31/327* (2013.01); *A61K 33/30* (2013.01); *A61K 45/06* (2013.01); *A61K 47/02* (2013.01)

(58) Field of Classification Search
None
See application file for complete search history.

(56) References Cited

U.S. PATENT DOCUMENTS

| 5,939,054 A * | 8/1999 | Msika et al. ..................... 424/59 |
| 6,001,378 A | 12/1999 | Desjonqueres |
| 6,475,526 B1 * | 11/2002 | Smith ........................... 424/642 |
| 6,686,392 B1 | 2/2004 | Avram |
| 2006/0275507 A1 * | 12/2006 | Hartman ....................... 424/642 |

FOREIGN PATENT DOCUMENTS

| CA | 2514381 | 1/2007 |
| EP | 0225831 | 6/1987 |
| EP | 1077064 A1 * | 2/2001 |
| FR | 2461744 | 2/1981 |
| JP | 62153215 | 7/1987 |
| WO | WO 2004066971 A1 * | 8/2004 |

OTHER PUBLICATIONS

Beauman, Genital Herpes: A Review, Am. Fam. Physician (2005), vol. 72, No. 8, pp. 1527-1534.*
Weisshaar et al., Pruritus: A Review, Acta Derm. Venereol. (2003), vol. 83, Suppl. 213, pp. 5-31.*
Rooney et al., Prevention of ultraviolet-light-induced herpes labialis by sunscreen, Lancet (1991), vol. 338, pp. 1419-1422.*

* cited by examiner

*Primary Examiner* — Abigail Fisher
*Assistant Examiner* — Frank Choi
(74) *Attorney, Agent, or Firm* — Ladas & Parry LLP

(57) ABSTRACT

A dermatological composition containing an association of peroxidized lipids; and zinc in mineral form or zinc compound compatible with dermatological use, formulated for topical application on the skin or the mucous membranes, is disclosed compatible with dermatological use. The composition may be used as a medical device to assist in healing and/or reconstitution of a damaged epidermis and/or to act as an analgesic agent on the skin or the mucous membranes, in particular in the treatment of the symptoms of herpes, pruritus, itching, irritations, eczema, burns, and most particularly in the treatment of labial or genital herpes.

25 Claims, 6 Drawing Sheets

FIG.3 Variation of burning score as a function of treatments

FIG.4 Variation of the sum of subjective scores as a function of treatments

FIG.5 Variation of itching

FIG.6 Variation of pricking

DERMATOLOGICAL COMPOSITIONS CONTAINING AN ASSOCIATION OF PEROXIDE LIPIDS AND ZINC, AND USES THEREOF IN PARTICULAR IN THE TREATMENT OF LABIAL AND/OR GENITAL HERPES

BACKGROUND OF THE INVENTION

The present invention relates to novel dermatological compositions containing an association of peroxidized lipids and zinc, and to uses thereof, in particular in the treatment of herpes.

DESCRIPTION OF RELATED ART

Herpes is a disorder that is very frequent, with manifestations that usually amount to a particular sequence of cutaneous/mucous membrane symptoms: primary infection; latency; multiple recurrences. Herpes lesions heal spontaneously, but they are characterized by being unattractive and by functional symptoms that give rise to discomfort. The cause is the herpes simplex virus (HSV). It is a DNA virus of size in the range 150 nanometers (nm) to 2000 nm. Two antigen types can be distinguished, HSV1 that usually infects the upper portion of the body (the main cause of labial herpes), and HSV2 that gives rise to herpes of the genital region.

Genital herpes is a common sexually transmissible disease. It affects 2 million people in France. Its symptoms are painful and recurring and they can interfere with the sex life of patients. The primary infection with herpes simplex virus begins 7 to 21 days after the infecting sexual contact. It is very spectacular and is manifested:

in man by balano-posthitis with urethritis; and
in woman by febrile acute vulvo-vaginitis with meatitis or cervicitis (disease of the urinary meatus or of the neck of the uterus).

Genital herpes is generally due to the herpes simplex virus of type 2 (HSV2), but HSV1 (implicated in labial herpes) may also be the cause. There also exist numerous asymptomatic forms of genital herpes (half of infected patients do not present any symptoms).

A herpes attack follows several stages: at the location of the cutaneous eruption the patient feels fleeting burning and itching; 24 to 48 hours later, small vesicles appear that are grouped together in bunches in the regions involved. General symptoms may be present (fever, indisposition). Several days later, the vesicles burst to leave small painful oozing erosions; thereafter crusts appears indicating that the attack is coming to an end after a duration of 4 to 8 days.

In women the mucous membranes involved are the vulva, the anal region, and the opening of the vagina; in man the glans, the sheath, the neck of the glans, and the anal region. A herpes lesion is painful, does not rest on an indurate base, and is accompanied by adenopathies. It is contagious for 2 weeks.

After a first attack of genital herpes, 50% to 70% of patients suffer no further manifestations of herpes. The others present frequent relapses as a result of trigger factors: stress, menstruation, flu, corticotherapy. At the time of an attack, the virus that has remained latent in the lymphatic ganglia returns to the skin along nerves and gives rise to lesions. Recurrences occur in the form of vesicles on the penis, the vulva, the neck of the uterus, and sometimes also on the buttocks or the legs. They give rise to local pain that the patient learns to recognize. The greater the severity of the primary infection, the more patients tend to present recurrences. In the long term, recurrences tend to become less frequent.

There exist treatments that treat an attack, but that do not enable the virus to be eliminated, the virus remaining in the latent state in the lymphatic ganglia between flare-ups. Such treatments rely mainly on using antiviral substances applied locally (creams or gels) or orally (tablets or drinkable solutions).

The purpose of treating a flare-up of labial herpes and indeed genital herpes is to reduce the functional symptoms, to shorten the time it takes to recover, and while it lasts, to reduce contagion. The local antiviral treatments that are generally used (creams based on 5% acyclovir, such as Zovirax®) can accelerate recovery, but they do not act on the functional symptoms that can be very incapacitating.

In the Applicant's prior application FR 2 591 109 a medicinal composition is described that is based on hyperoxygenated natural oils of vegetable origin including peroxidized triglycerides (OGT) for treating herpes. By way of example, the oil may be selected from peanut oil, sweet almond oil, and safflower oil, see in particular claims 1 and 2. Nevertheless, that composition has subsequently been found not to be significantly effective in the treatment of herpes.

Zinc and certain zinc compounds such as zinc oxide and also zinc acetate, carbonate, sulfate, phosphate, chloride, distearate, and gluconate are well known for their antiseptic or antifungal properties and for their action against itching.

Thus, zinc oxide lotions or creams have been used for a long time against itching or for treating diaper rash. Zinc oxide is also known for its weakly antifungal properties, and consequently it opposes the development of mycoses.

It is also known that zinc oxide presents a broad range of uses including some in the field of cosmetics, in particular for its sunscreen properties.

Certain ointments or lotions are known that contain zinc oxide, with the presence of the zinc oxide serving in particular to prevent the skin being irritated and assisting in returning skin to a good state.

Remedial compositions are also known for the skin that also present antibacterial properties and that contain zinc oxide, such compositions being in very widespread use, in particular for children suffering eczema or milk crusts.

SUMMARY OF THE INVENTION

A main object of the invention is to solve the technical problem consisting in providing a novel composition usable for local application as medicine for treating herpes in a manner that is more effective than previously known topical compositions.

Another main object of the invention is to solve the technical problem consisting in providing a novel composition capable of treating herpes more effectively, not only than a placebo, but above all than a positive control such as the acyclovir antiviral agent (Zovirax®) of worldwide reputation, or than peroxidized lipids used on their own.

Another main object of the invention is to solve the technical problem consisting in providing a novel composition capable of treating both labial herpes and genital herpes.

Another main object of the present invention is to solve the technical problem consisting in providing a novel composition capable of treating quickly and effectively the pain that is associated with labial or genital herpes.

A main object of the present invention is also to solve the technical problem consisting in providing a novel composition capable not only of treating pain but also secondary attacks of pain comprising burning, pricking, pruritus or itching, erythema, or indeed clinical symptoms accompanying an episode of herpes, mainly edema, ulceration, erosion, papules, vesicles, crusts.

More generally, a main object of the present invention is to provide a novel pharmaceutical formulation for assisting healing or regeneration of skin or mucous membrane and/or reconstitution of a damaged epidermis and/or to act as an analgesic agent on the skin or the mucous membrane and enabling for treating the skin for indications of the same kind as herpes and comprising pruritus, burning, in particular after radiotherapy treatment, UV burning, in particular as a result of exposure to the sun, itching, and irritation due to scratching.

Finally, a main object of the invention is to solve all of the above technical problems by means of a novel formulation that is simple, safe and reliable, stable, that is effective repetitively, and usable on an industrial and medical scale.

Tests performed by the inventor, initially with herpes, have revealed a synergy effect due to adding zinc or a zinc compound compatible with dermatological use to a topical composition containing peroxidized lipids or oxidized glycerol triesters (OGT), resulting in activity that is significantly more effective against herpes, in particular compared not only with a placebo, but also with a positive control constituted by medication including 5% acyclovir (Zovirax®) of worldwide reputation or compared with peroxidized lipids used on their own.

In addition, it has been discovered unexpectedly that this association of peroxidized lipids or OGT with zinc enables the preparation to be made to be more pasty and more adherent, thereby making it possible greatly to improve the adhesion of the protective film formed by the oxidized glycerol triesters and to improve the impregnation of spots, leading to a reduction in the appearance of functional symptoms and to an acceleration in the physical reconstruction of the damaged mucous membranes or cutaneous tissue.

Furthermore, a lesion due to labial or genital herpes comprises two main components in the course of its development:
  a lesion component, passing through the papule, vesicle stage, or even blisters with the presence of erythema and crusts in the final stage;
  a functional symptom component of pain, burning, that may be very incapacitating for the subject.

It has been found that the relief of these functional symptoms can be obtained equally well with labial and with genital herpes by applying to the portions of skin or mucous membranes that are involved compositions that comprise an association of peroxidized lipids and zinc or zinc compounds constituting the subject matter of the present invention.

Furthermore, another advantage of the presence of zinc or of its compounds or derivatives in the composition is that it participates in obtaining better conservation of the composition because of the well-known antibacterial properties of zinc and of its compounds or derivatives.

DETAILED DESCRIPTION OF THE INVENTION

Definitions

Herpes: herpes is a disease of viral origin that attacks either the skin or the mucous membranes of the face, in particular the lips, known as labial herpes, or else genital mucous membranes known as genital herpes, and presents a quasi-systematic recurrency factor. The factor that triggers a herpes attack is often of emotional origin, but may also be of physiological origin such as menstruation and may also have other external causes such as exposure to the sun, known as solar herpes, etc. Herpes is characterized by the presence of painful pustules that are open and oozing, usually accompanied with very marked inflammation.

Labial herpes: in the present description and in the claims, the term "labial herpes" designates a herpes that is localized on the face and in particular on the mucous membranes of the face, and particularly the lips.

Genital herpes: in the present description and in the claims, the term "genital herpes" designates a herpes that is located on the skin below the belt and that may include both the buttocks and the genital mucous membranes.

Dermatological composition: in the present description and in the claims, the term "dermatological composition", designates a composition for topical application to the skin, the dermis, or the mucous membranes, and that generally does not require Marketing Authorization (MA).

Pharmaceutical composition: in the present description and in the claims, the term "pharmaceutical composition", designates a composition that is recognized as a medicine and that thus requires Marketing Authorization (MA). In the context of the invention, the pharmaceutical composition is particularly intended for topical application on the skin, the dermis, or the mucous membranes.

Peroxidized lipids: in the present description and in the claims, the term "peroxidized lipids", designates peroxidized fats belonging to the family of hyperoxygenated natural oils. This hyperoxygenation is generally obtained by oxygen saturation and by intensive and controlled exposure to ultraviolet radiation so as to present a given peroxidation level. Such a lipid of vegetable origin is to be found amongst natural oils of vegetal origin as described below.

Zinc: in the present description and in the claims, the term "zinc", designates a zinc component selected from zinc in a mineral form or metallic zinc, and from a zinc compound that is dermatologically compatible. Non limitative Examples thereof are given later on in this specification.

Thus, the invention relates both to dermatological and/or pharmaceutical compositions for topical application.

As a result, in a first aspect, the invention provides novel dermatological and/or pharmaceutical compositions for topical application containing, as active agents or essential ingredients, an association of peroxidized lipids and of a zinc component selected from zinc in a mineral form and from a zinc compound compatible with dermatological use.

In the meaning of the invention, the term "active agents or essential ingredients" should be understood as indicating that the peroxidized lipids and the zinc component are active agents or main ingredients of active agents of the composition. In the context of a composition in the form of an oily gel, their total percentage by weight is generally at least 50%, in particular at least 55%, and preferably at least 70%. Furthermore, in the context of a composition in the form of a cream, made from an emulsion, in particular an oil-in-water type emulsion, the oily phase of said emulsion comprises 1% to 25% by weight peroxidized lipids relative to said composition.

The presence of the peroxidized lipid enables a lipid film to be formed on the skin or the mucous membrane for treatment, which film acts as a genuine dressing that provides shelter, thereby accelerating natural regeneration of tissue and consequently facilitating healing.

The zinc or the zinc compound serves simultaneously to improve the healing effect of the composition and to further improve the adhesion of the film on the skin or the mucous membrane.

It also contributes to better preservation of the composition.

These compositions developed most particularly for treating the symptoms of herpes, in particular labial or genital herpes, may also be used in any dermatological applications where it is desired to obtain improved healing or reconstitution of damaged epidermis or analgesic action on the skin.

A particular advantage of compositions of the invention is that in their presently preferred formulations, they do not give rise to any pharmacological, metabolic, or immunological effects, since they do not contain pharmacological compounds and they are constituted essentially by peroxidized lipids, namely oxidized glycerol triesters, and also zinc or zinc components or zinc compounds because of its synergistic effect improving the galenic dosage form and protecting the composition, with the other ingredients being constituted essentially by flavorings or fragrances, preservative agents, or agents for adjusting the viscosity of the composition in order to improve topical application on the skin or the intended mucous membranes.

A particular advantage of compositions of this type and of the mode of action implemented on application thereof (forming a lipid film on the region for treatment) is that they are particularly advantageous at a time when it is most particularly desirable to find methods of treatment that are as little aggressive as possible for the organism. These compositions also make it possible to satisfy the regulations of the European Community relating to medical devices, and of American organizations such as the Food and Drug Administration (FDA) relating to medical devices or to monograph products.

In a particular embodiment of the invention, the peroxidized lipids may have a peroxidation level lying in the range 5 to 600 milliequivalents per kilogram (kg) of peroxidized lipids.

In another particular embodiment of the invention, the zinc component is present either in mineral form or metallic form, or in the form of a zinc compound compatible with dermatological application, said composition being formulated for topical application on the skin or the mucous membranes.

Thus, in yet another particular embodiment of the invention, the invention provides a topical dermatological and/or pharmaceutical composition in the form of a gel, and comprising an association in relative percentages by weight of:
 peroxidized lipids or OGT from 50% to 99%;
 zinc component from 1.0% to 25%.

Thus, in yet another particular embodiment of the invention, the invention provides a topical dermatological and/or pharmaceutical composition in the form of a gel comprising, in relative percentages by weight:
 peroxidized lipids or OGT from 50% to 95%;
 zinc component from 1.0% to 25%; and a gelling agent, comprising silicon dioxide, from 1% to 10.0%.

An example of silicon dioxide is colloidal silica, as available in particular on the market under the name Aerosil®.

In yet another particular embodiment of the invention, the invention provides a topical dermatological and/or pharmaceutical composition in the form of a gel, comprising, in relative percentages by weight:
    peroxidized lipids from 50% to 95%;
    zinc component from 1.0% to 25%;
    a gelling agent, comprising silicon dioxide, from 1% to 10.0%;
    optionally a preservative agent from 0.1% to 1.0%; and
    optionally flavoring from 0.5% to 5%.

According to a particular feature, in all embodiments of the invention, the balance up to 100% of the composition of the invention is generally constituted by peroxidized oils in a gel formulation, or by water in a cream formulation.

As an example of a preservative agent, it is possible to use at least one paraben, such as propylparaben.

In addition to the active agents or essential ingredients, i.e. the peroxidized oil and the zinc component, and optionally water, the composition of the invention may contain various additives such as, in particular, fragrances or flavorings selected as a function of the application of the composition, preservative agents, or agents for controlling the viscosity of the composition.

As an example of flavorings, it is possible to use all types of flavoring such as orange, grapefruit, mint, and in particular the composition may include as flavoring, and by weight:
    orange-grapefruit: 2.5%
    mint flavoring: 1.5%.

The composition may also contain various formulation additives for the purpose in particular of improving the galenic dosage form, for facilitating application, or for improving the protection of the composition.

In conventional manner, such formulation additives are emulsifiers, surfactants, wetting agents, emollients, preservatives, or antioxidants.

As an example of a preservative agent, it is possible to use at least one paraben such as propylparaben.

The peroxidized lipids used for preparing compositions of the invention result from peroxidizing unsaturated fats. The degree of peroxidation is measured using the standard ISO 3960.

For preparing compositions of the present invention, peroxidized lipids should be selected that present a peroxidation level lying in the range 5 to 600 milliequivalents per kg, preferably in the range 30 to 500 milliequivalents per kg.

In even more advantageous manner, this level of peroxidation lies in the range 50 to 300 milliequivalents per kg, and more preferably in the range 50 to 150 milliequivalents per kg.

The preferred peroxidized lipids used in the invention result from peroxidizing lipids or fats of natural origin, preferably of vegetable origin, more preferably lipids derived from a natural vegetable oil.

As examples of natural oils that may be selected in the invention, mention is made of sweet almond oil, hazelnut oil, peanut oil, corn oil, grapeseed oil, sesame oil, and safflower oil. It is also possible to use a mixture of these oils.

In a particularly preferred variant of the invention, peroxidized corn oil is selected and most particularly a corn oil presenting a peroxidation level lying in the range 5 to 600 milliequivalents per kg.

In terms of majority ingredients or active principles relative to the total of active principles, generally representing at least 80% by weight, the peroxidized lipids used in the invention are advantageously constituted by triglycerides satisfying the formula:

in which the radicals R are represented in the majority by partially peroxidized $C_{18}$ unsaturated acids, as a function of the peroxidation level of said lipid.

As explained above, compositions of the invention contain a zinc component, which may be in the form either of metallic zinc, or in the form of a dermatologically acceptable zinc compound known in particular for its protective and covering properties, and thus facilitating healing and reducing pain and inflammation.

As zinc compounds that are dermatologically compatible and therefore acceptable for inclusion in the composition of the invention, mention may be made, as non-limitative examples of zinc oxide, zinc acetate, zinc carbonate, zinc sulfate, zinc phosphate, zinc chloride, zinc stearate or distearate, and zinc gluconate.

It is preferable to select zinc acetate, zinc carbonate, or zinc oxide.

In an advantageous variant of the invention, the zinc component is present in the composition in micronized form, thus enhancing application of the composition on the skin or the mucous membrane concerned.

The zinc component is advantageously in the composition at a concentration that is commonly used in dermatological applications of zinc.

Thus, the composition of the invention advantageously contains 0.1% to 25% by weight of zinc component, preferably 1% to 25% of zinc oxide or 0.1% to 2% of zinc acetate or 0.2% to 2% of zinc carbonate.

Compositions of the invention are advantageously prepared in the form of a gel or a cream.

When the composition is in the form of a gel, it is generally an oily gel.

The peroxidized lipids constitute the oil of the oily gel in which the peroxidized oil content lies in particular in the range 50% to 95% by weight. The gel may also contain a viscosity agent enabling the desired viscosity to be obtained for good topical application of the gel. The viscosity agent is preferably colloidal silica, and the gel should also contain the desired proportion of zinc component. A mixture of the peroxidized lipids and of zinc component is made previously to the operations of gelification or of manufacture of the emulsions such as creams, ointments. It may optionally contain one or more preservatives and/or a fragrance or a flavoring, selected as a function of the type of application intended.

Naturally, the fragrance or flavoring should be selected as a function of the intended type of application.

For example, for treating labial herpes, it is preferable to select a flavoring of the food flavoring type. The use of such flavorings or fragrances should be avoided when treating genital herpes.

When the composition is in the form of a cream, prepared from an emulsion, the emulsion is in particular an oil-in-water type emulsion. In such an emulsion, the oily phase is constituted by peroxidized lipids and advantageously constitutes 1% to 25% by weight of said composition. It is also possible in general manner for it to contain any formulation additive as conventionally used in the field.

As set out above, the composition of the invention presents the advantage of satisfying the definition of a medical device in accordance with the European regulation in force 93/42/EEC.

Thus, the composition of the invention may be used as a medical device in very numerous applications where it is desired in particular to enhance healing or regeneration of the skin, in particular by forming a protective film on the skin.

Thus, the medical device is most particularly intended for enhancing renewal of cells of the dermis and thus assist in healing or regenerating skin or mucous membrane and/or reconstitution of the damaged epidermis and/or for acting as an analgesic agent on the skin or the mucous membrane.

In a second aspect, the invention also covers the use of an association of peroxidized lipids and of zinc component, selected from metallic zinc and a zinc compound compatible with dermatological use, in the preparation of a medical device as defined above or as resulting from the description below, said medical device being for use in assisting healing or regenerating skin or mucous membrane and/or reconstitution of a damaged epidermis and/or to act as an analgesic agent on the skin or the mucous membrane.

In particular, said medical device is for use in treating the symptoms of herpes: pain, burning, itching, pricking, edema, ulceration/erosion, erythema, papules, vesicles, crusts.

According to a variant embodiment, said medical device is for performing a treatment selected from treating symptoms of burns, treating burns of post therapy or induced by pre-cancerous or cancerous treatments of skin, treating domestic burns, and burns induced by exposure to the sun.

According to another variant embodiment, said medical device is for the treatment of symptoms of Chronic itching sine materia, pricking and scratching lesions.

According to another embodiment, said medical device is for use in treating labial herpes.

According to a further embodiment, said medical device is for use in treating genital herpes.

According to a third aspect, the invention also covers a method of treating at least one body area in need thereof, selected from a skin area, an epidermis area and a mucous membrane area comprising applying topically on said body area a composition as defined above or as resulting from the description below together with the drawings, in which FIGS. 2 to 12 form an integral part of the invention; and that notably for the purpose of assisting healing or regeneration of skin or mucous membrane and/or reconstitution of a damaged epidermis and/or to act as an analgesic agent on the skin or the mucous membrane.

In a variant embodiment, the treatment method is for treating the symptoms of herpes: pain, burning, itching, pricking, edema, ulceration/erosion, erythema, papules, vesicles, crusts, According to a variant embodiment, said method is for performing a treatment selected from treating symptoms of burns, treating burns of post therapy or induced by pre-cancerous or cancerous treatments of skin, treating domestic burns, and burns induced by exposure to the sun.

According to another variant embodiment, said method is for the treatment of symptoms of Chronic itching sine materia, pricking and scratching lesions.

According to another embodiment, said medical device is for use in treating labial herpes.

According to a further embodiment, said medical device is for use in treating genital herpes.

In yet another variant implementation, this treatment method comprises applying the composition three to five times per day on the area of the skin or the mucous membrane in need thereof.

By forming a protective film on the various lesions of the skin or the mucous membranes concerned while it is being applied, the composition of the invention is particularly applicable for assisting healing or regeneration of skin or mucous membrane and/or reconstitution of a damaged epidermis and/or to act as an analgesic agent on the skin or the mucous membrane; and in particular for treating the symptoms of herpes: pain, burning, itching, pricking, edema, ulceration/erosion, erythema, papules, vesicles, crusts, symptoms of burns, burns of post therapy or induced by pre-cancerous or cancerous treatments of skin, domestic burns, burns induced by exposure to the sun, for the treatment of symptoms of Chronic itching sine materia, pricking, and scratching lesions.

As can be seen from the examples, this composition is particularly useful in treating the symptoms of labial or genital herpes.

In all of the intended applications, better adhesion has been observed of the film that is formed on the damaged skin or mucous membrane, which adhesion results from the presence of zinc or zinc component.

EXAMPLES

In the examples below, the proportions given are expressed as percentages by weight, temperatures in ° C., and the pressure is atmospheric pressure. Furthermore, the balance up to 100% is always constituted by peroxidized lipids or by water when the galenic dosage form is a cream.

Example 1

Comparative Composition Code PB14 According to FR 2 591 109

A comparative composition was prepared in accordance with the example of the Applicant's prior patent FR-2 591 109B1, page 5, lines 5 to 8, specifically a gel having the following composition:

| | |
|---|---|
| hyperoxygenated safflower oil: | 90.7% |
| silicon dioxide in the form of micronized silica sold under the trademark Aerosil 300 ® by the supplier Degussa: | 6.8% |
| fragrance: | 2.5% |

This composition has code name PB14.

Peroxidized safflower oil presents a level of peroxidation lying in the range 30 to 300 expressed in milliequivalents per kg.

The examples below use peroxidized corn oils (maize oils) presenting peroxidation levels lying in the range 50 to 600 expressed as milliequivalents per kg.

Example 2

Composition for Treating Labial Herpes

This composition was prepared using the following ingredients, in the conventional manner, and has the code CS20:

| Ingredients, code CS20 | % |
|---|---|
| Peroxidized corn oil | 87.8% |
| Micronized zinc oxide | 1.0% |
| Silicon dioxide gelling agent* | 7.0% |
| "Orange-grapefruit" fragrances | 2.5% |
| "Mint" fragrance | 1.5% |
| Propylparaben preservative agent | 0.2% |

*Aerosil 300 ® colloidal silica from Degussa

Example 3

Composition for Treating Genital Herpes

This composition was prepared using the following ingredients, in the conventional manner, and has the code CS21:

| Ingredients code CS21 | % |
|---|---|
| Peroxidized corn oil | 91.8% |
| Micronized zinc oxide | 1.0% |
| Silicon dioxide gelling agent* | 7.0% |
| Propylparaben preservative agent | 0.2% |

* Aerosil 300 ® colloidal silica from Degussa

Example 4

Effectiveness Tests 4-1. Test of the Effectiveness of the PB14 Comparative Composition of Example 1

The tests were performed as follows:

Five applications per day for thirteen days for the comparative composition of Example 1, code PB14.

Two groups of 20 patients per group, inclusion characteristics: patients of both sexes aged more than 15 years presenting two recurrent bouts of herpes with at least two recurrences in the preceding year and at the same location.

Characteristics for non-inclusion:
primary infection;
doubtful clinical symptoms;
patients under antiviral treatment;
diabetes, pregnancy;
immunodeficient patients.

Placebo and one group with the product under test.

Figure 1:
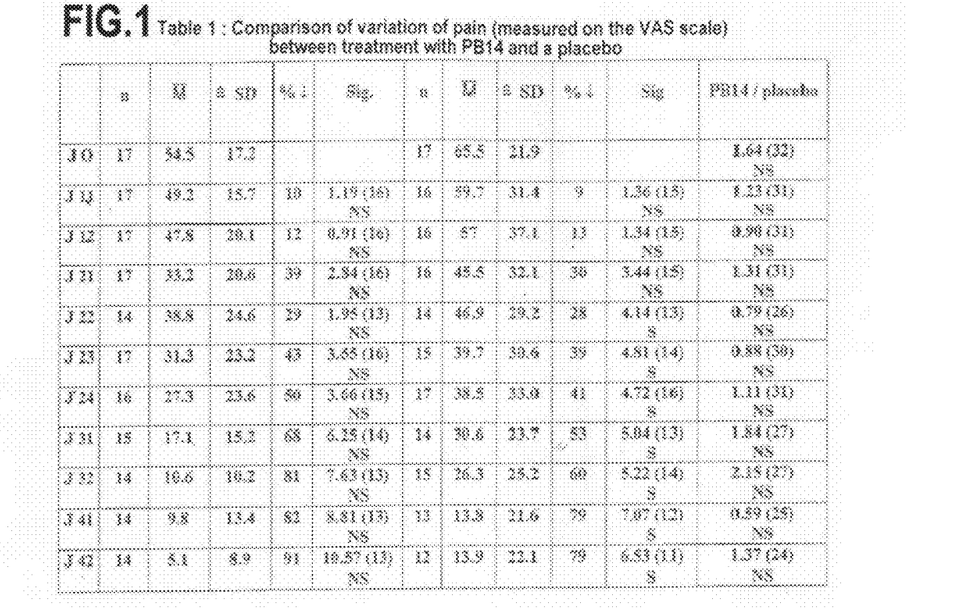
FIG. 1 is a table showing comparative variation in pain between treatments with the comparative product known as PB14, in accordance with Example 1 below and described on page 5, lines 5 to 8 of prior FR-2 591 109 B1 (equivalent to EP 0 225 831) in the name of the Applicant, and with 15 the placebo; pain being measured on the VAS scale.

The results for comparative variation of pain, measured on the VAS, between the treatments with the comparative product named PB14, in accordance with above-described Example 1 and page 5, lines 5 to 8 of prior FR-2 591 109 B1 in the name of the Applicant, and the placebo are set out in Table 1 given in FIG. 1.

The "VAS" method is a method of self-evaluating pain that is internationally recognized by practitioners, relative to extreme points: intolerable pain and no pain at all. On a straight line having a length of 10 centimeters (cm), the patient places a mark between those two extremes.

From Table 1 it can be seen that with PB14 peroxidized oils used on their own, the results of clinical studies relating to sedating the pain of herpes regions were disappointing, without any significant difference being established between PB14 and the placebo from D0 to D42.

4-2 Tests of the Effectiveness of the CS20 and CS21 Compositions of the Invention of Examples 2 and 3

The preparation of the CS20 product, of a composition different from the prior product PB14, justified clinical research of results that ought to correspond to the expectations of patients concerning functional and clinical symptoms of herpes, in particular compared with the world-renowned major product with an antiviral effect that includes acyclovir (Zovirax®) that is claimed to shorten the duration of a herpes flare-up, and that was used as a positive control.

It is well known that relieving the pain and the burning that accompany a flare-up of herpes are major criteria for assessing effectiveness.

The object of the invention was thus to find a product having beneficial action essentially directed to this purpose. That is why the clinical trials referenced in this specification correspond to a protocol in which relieving pain and burning are the main criteria. The clinical symptoms accompanying the episode of herpes, mainly edema, ulceration, erosion, papules, vesicles, and crusts, were also taken into account.

The protocol of therapeutic tests on the herpes lesion recommends five applications per day for fifteen days with the composition of the invention, either Example 2, code CS20, for Labial herpes, or Example 3, code CS21, for genital herpes; and also for the placebo and for the medicine containing acyclovir, as constituted by Zovirax®.

For Labial Herpes, Composition of Example 2, CS20

Three groups of 35 patients per group, inclusion characteristics: patients of both sexes aged more than 18 years presenting recurrent herpes with at least four flare-ups during the preceding year at the same location.

Characteristics for non-inclusion:
primary infection;
doubtful clinical symptoms;
patients under antiviral treatment;
diabetes, pregnancy;
immunodeficient patients.

For Genital Herpes, Composition of Example 3, CS21

Three groups of 20 patients per group, inclusion characteristics: patients of both sexes aged more than 18 years presenting recurrent herpes with at least four flare-ups during the preceding year at the same location in the genital region of man and woman.

Characteristics for non-inclusion:
primary infection;
doubtful clinical symptoms;
patients under antiviral treatment;
diabetes, pregnancy;
immunodeficient patients.

For Each Test
One group received the placebo;
One group received the positive control Zovirax®; and
One group received the product of the invention code CS20 or CS21.

The results given in FIGS. 2 to 12 are the statistical means of each group with a significance level smaller than 0.05 for pain as for burning, demonstrating the unexpected superiority of the composition of the invention compared not only with the placebo, but also with the positive control constituted by the antiviral medicine that is the majority prescription for herpes, i.e. 5% acyclovir in the form of a cream (Zovirax®).

In FIGS. 2 to 12, a star next to a particular point marks a point of significant difference between the product of the invention CS20 compared with Zovirax® and/or the placebo.

Figure 2:
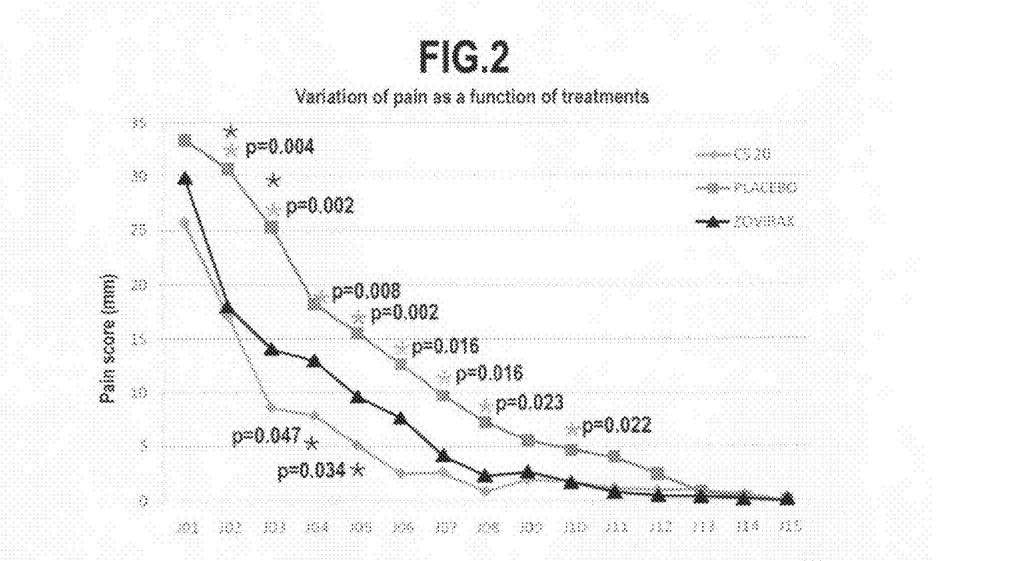
FIG. 2 shows the results of the test for variation in pain as a function of the treatments respectively using the placebo, curved plotted with squares, using the positive control Zovirax®, curve 20 plotted with triangles, and using the product of the invention code CS20, curve plotted with lozenges, with days D01 to D15 along the abscissa; and with the pain score expressed in millimeters on the basis of a pain evaluation rule, the only recognized method of evaluating 25 pain, being plotted on a scale of 0 to 35 up the ordinate.

Thus, FIG. 2 shows a significant difference concerning pain for the product of the invention CS20 relative to the placebo from D2 to D12; and relative to Zovirax® from D4 to D5.

Figure 3:
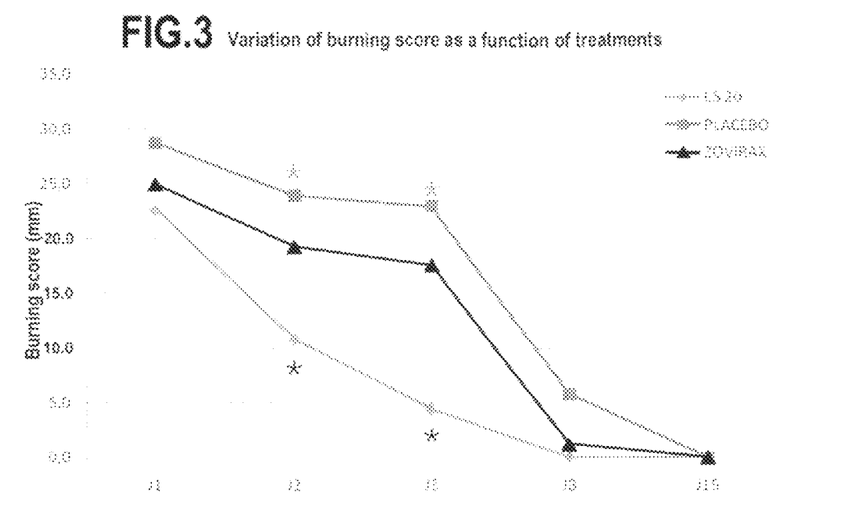
FIG. 3 shows variation in the burning score as a function of the treatments from D1 to D15 plotted along the abscissa as a function of the burning score in 30 millimeters on the pain scale 0.0 to 35.0 plotted up the ordinate, comparing the placebo, plotted using squares, the positive control Zovirax®, plotted using triangles, and the product of the invention code CS20, plotted using lozenges.

FIG. 3 shows a significant difference concerning burning for the product of the invention CS20 relative to the placebo on D2 with a significance p value of 0.004, and on D3 with a significance p value of 0.000; and relative to Zovirax® on D2 with a significance p value of 0.033, and on D3 with a significance p value of 0.005.

Figure 4:
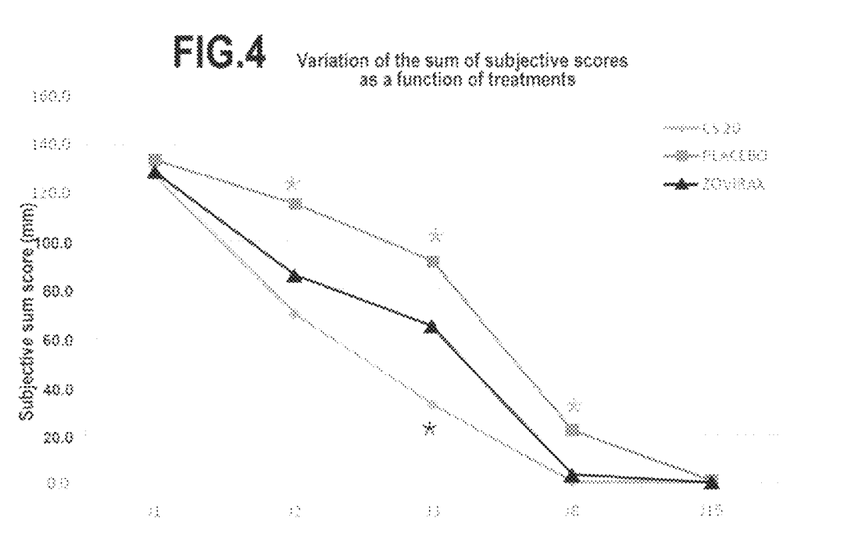
FIG. 4 shows the curve of variation in the sum of the subjective scores as a function of the treatments subjective sum score being plotted in millimeters from 0.0 to 160.0 up the ordinate, comparing the placebo, the positive control Zovirax®, and the products of the invention with code CS20.

FIG. 4 shows a significant difference for the sum of the subjective scores as a function of the treatments for the product of the invention CS20 relative to the placebo on D2 with a significance p value of 0.008, and on D3 with a significance p value of 0.000; and compared with Zovirax® on D3 with a significance p value of 0.033.

Figure 5:
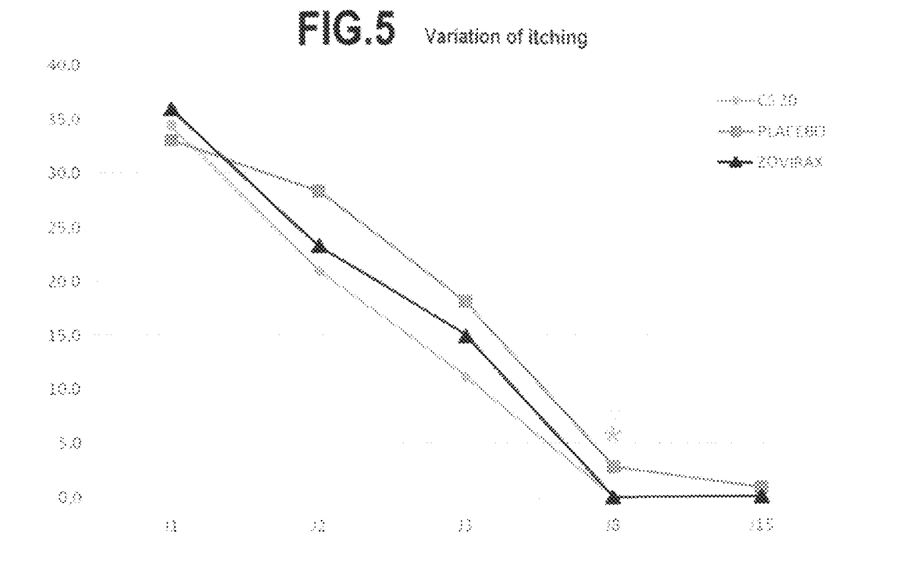
FIG. 5 shows the curve of variation in itching (pruritus) from D1 to D15 plotted along the abscissa as a function of the itching variation score plotted up the ordinate, on a scale from 0.0 to 40.0 comparing the same placebo, the same positive control Zovirax®, and the product of the invention code CS20.

FIG. 5 shows variation of itching where the product of the invention CS20 and Zovirax® are significant compared with the placebo on D8.

Figure 6:
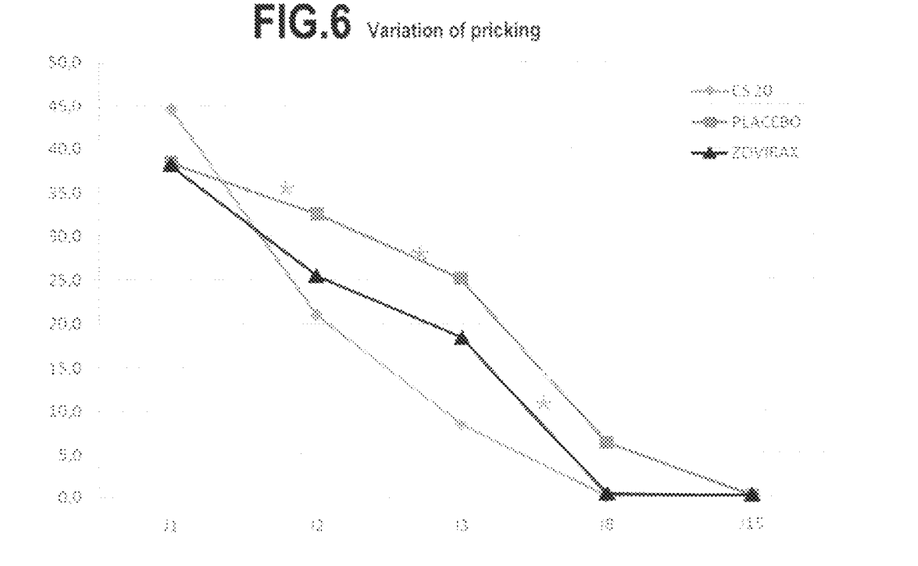
FIG. 6 shows the variation in pricking from D1 to D15 plotted along the abscissa as a function of the score for variation in pricking plotted up the ordinate on a scale marked from 0.0 to 50.0, comparing the same placebo, the same positive control Zovirax®, and the product of the invention code CS20.
Figure 7:
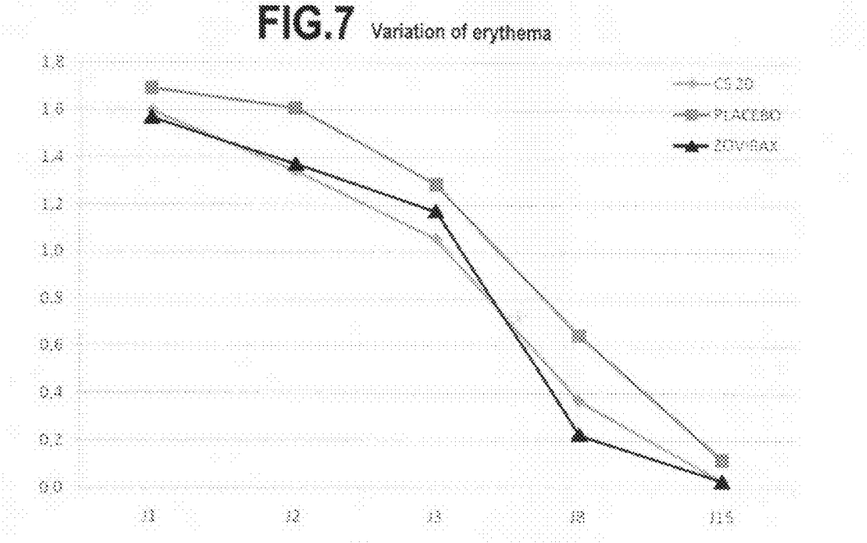
FIG. 7 shows the curve for variation in erythema (rash) from D1 to D15 plotted along the abscissa, as a function of the score for variation in erythema plotted up the ordinate on a scale marked 0.01 to 1.8, respectively for the placebo, curve plotted using squares; and the same positive control Zovirax®, curve plotted using triangles, and CS20, curve plotted using lozenges.
Figure 8:
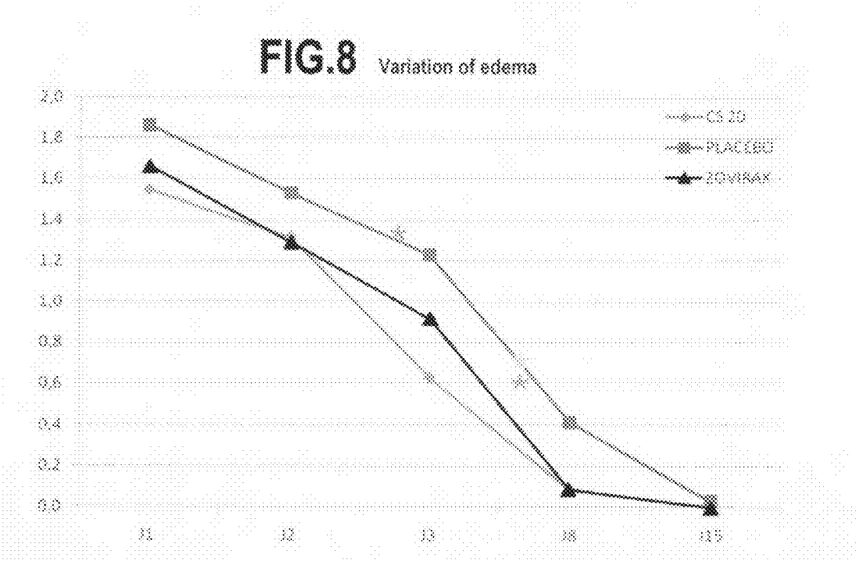
FIG. 8 shows the curve for variation of edema from D1 to D15 plotted along the abscissa as a function of the score for variation in edema plotted up the ordinate on a scale marked from 0.0 to 2.0, for the same placebo, the same positive control Zovirax®, and the product of the invention code CS20.
Figure 9:
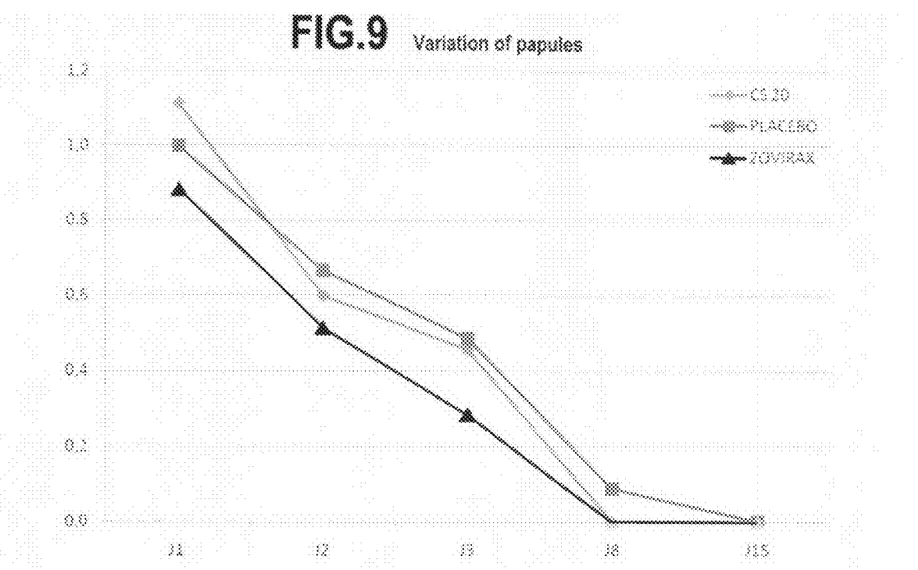
FIG. 9 shows the curve for variation in papules from D1 to D15 plotted along the abscissa as a function of the score for variation of the papules plotted up the ordinate on a scale marked from 0.01 to 1.2, using the same placebo, the same positive control Zovirax®, and the product of the invention code CS20.
Figure 10:
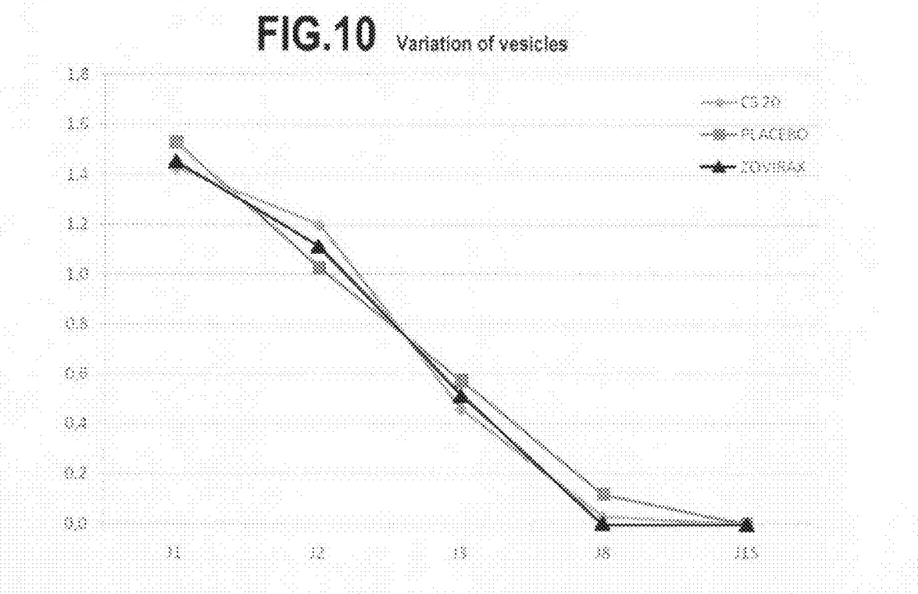
FIG. 10 shows the curve for variation in vesicles from D1 to D15 plotted along the abscissa as a function of the score for variation of vesicles plotted up the ordinate on a scale from 0.01 to 1.8 for the same placebo, the same positive control Zovirax®, and the product of the invention code CS20.
Figure 11:
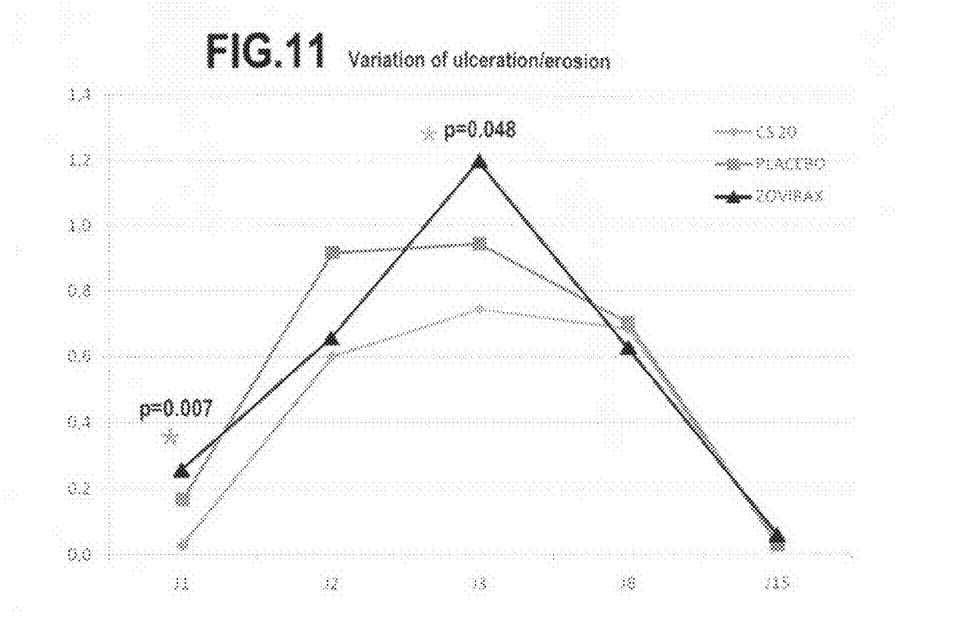
FIG. 11 shows the curve for variation in ulceration/erosion from D1 to D15 plotted along the abscissa as a function of the score for variation in ulceration/erosion on a scale from 0.01 to 1.4, respectively for the same placebo, the same positive control Zovirax®, and the product of the invention code CS20.
Figure 12:
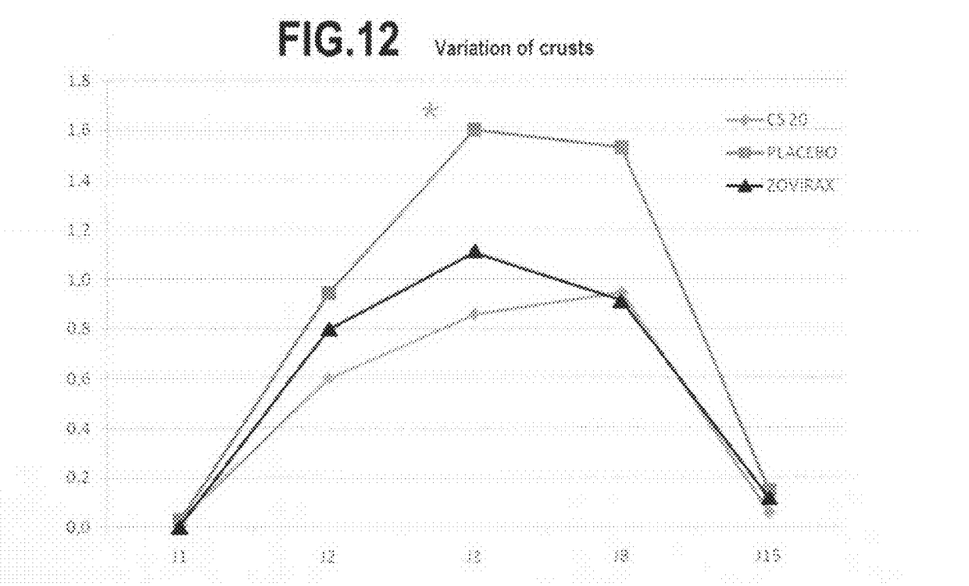
FIG. 12 shows the curve for variation in crusts from D1 to D15 plotted along the abscissa as a function of the score for variation in crusts plotted on a scale from 0.01 to 1.8 up the ordinate for the same placebo, the same positive control Zovirax®, and the product of the invention code CS20.

As can also be seen from FIGS. 2 to 12, in addition to functional symptoms, the study revealed significant results with the Example 2 composition of the invention, the product CS20 compared with at least the placebo, for clinical symptoms comprising:
 variation of itching on D8, FIG. 5;
 variation of pricking on D2, D3, D8, FIG. 6;
 variation of erythema towards D8, FIG. 7;
 variation of edema at D3 up to D8, FIG. 8;
 variation of ulceration/erosion relative to Zovirax® on D1 with a significance p value less than 0.007 and on D3 with a p value less than 0.048, FIG. 11; and
 variation of crusts with a significance p value of less than 0.009 relative to the placebo on D3.

As can also be seen from Table 2 below, the CS20 product of the invention is highly significant for sedating pain compared with the placebo and also compared with the positive control constituted by the antiviral medicine usually prescribed against herpes, namely 5% acyclovir in the form of a cream (Zovirax®).

TABLE 2

Analysis of the question put in the self-assessment questionnaire on D15 to each person in all of the groups tested
Reminder of the question:

| Compared with your experience of herpes lesions | Select a reply |
| --- | --- |
| Q1 reduction: Would you say that the treatment has reduced the painful sensations of herpes? | 2 = agree completely<br>1 = agree somewhat<br>0 = no opinion<br>−1 = disagree somewhat<br>−2 = disagree completely |

The distribution of replies is given in the table below:

|  | CS20 | PLACEBO | ZOVIRAX | TOTAL |
| --- | --- | --- | --- | --- |
| −2 | 0 | 6 | 1 | 7 |
| −1 | 3 | 5 | 4 | 12 |
| 0 | 0 | 2 | 0 | 2 |
| 1 | 3 | 11 | 16 | 30 |
| 2 | 29 | 10 | 14 | 53 |
| Total | 35 | 34 | 35 | 104 |

The statistical projection of these results is as follows:

|  | CS20 vs. placebo | Zovirax vs. placebo | CS20 vs. Zovirax |
| --- | --- | --- | --- |
| Q1 reduction | $P < 0.000$ for CS20 | $P = 0.123$ (ns) | $P = 0.002$ for CS20 |

In conclusion, the Example 2 composition of the invention, CS20, is very significantly better than the placebo and even than the positive control constituted by the antiviral medicine usually prescribed against herpes, namely 5% acyclovir in the form of a cream (Zovirax®) with a significance level of 0.007.

Similar results are expected for genital herpes, using the Example 3 composition, CS21.

Given these results, the invention is applicable to treating the skin or the mucous membranes for indications of the same kind, comprising: treating the symptoms of herpes: pain, burning, itching, pricking, edema, ulceration/erosion, erythema, papules, vesicles, crusts, and also domestic burns, burns after radiotherapy, or burns as a result of exposure to the sun.

Example 5

Dermatological and/or Pharmaceutical Composition for Treating Labial Herpes

| Ingredients, code CS20 | % |
| --- | --- |
| Peroxidized corn oil | 87.8% |
| Micronized zinc oxide | 1.0% |
| Silicon dioxide gelling agent* | 7.0% |
| "Orange-grapefruit" fragrances | 2.5% |
| "Mint" fragrance | 1.5% |
| Propylparaben preservative agent | 0.2% |

*Aerosil 300 ® colloidal silica from Degussa

This composition was applied three to five times per day with light massage on the zone concerned for six consecutive days after the appearance of the first painful symptoms. It was found that the pain ceased quickly and the herpes spot disappeared after three to four days of treatment. The herpes attack was attenuated and its duration significantly shortened.

This test was performed on 35 volunteers.

Example 6

Dermatological and/or Pharmaceutical Composition for Treating Genital Herpes

The composition contained:

| Ingredients code CS21 | % |
| --- | --- |
| Peroxidized corn oil | 91.8% |
| Micronized zinc oxide | 1.0% |
| Silicon dioxide gelling agent* | 7.0% |
| Propylparaben preservative agent | 0.2% |

*Aerosil 300 ® colloidal silica from Degussa

This composition was applied three to five times per day with light massage on the zone concerned for eight consecutive days from the appearance of the first painful symptoms.

This test was performed on 20 volunteers.

Example 7

Dermatological Cream Based on Peroxidized Lipids and Zinc Oxide for Treating Burns, Pruritus and Itching A dermatological cream may be formulated based on peroxidized lipids and on zinc oxide for treating burns, pruritus, and itching having the following composition:

| Ingredients | % |
|---|---|
| Peroxidized corn oil | 20.0% |
| Zinc oxide | 4.0% |
| Salcare ®* excipient | 2.00% |
| Paraben preservative agent | 0.5% |
| Kathon CG ®** excipient | 0.05% |
| Demineralized water | qsp 100% |

*Salcare is a cosmetic agent from Ciba serving to control viscosity and giving a white color.
**Kathon CG ® is a cosmetic agent from Seppic, also serving to control viscosity and giving rise to a white color.

This cream may be applied two to three times per day for 10 days on lesions due to scratching itches or pruritus, and on domestic burns, burns as a result of radiotherapy, or burns due to exposure to the sun.

What is claimed is:

1. A topical oily composition comprising an effective amount for treatment of symptoms of labial or genital herpes of from 50% to 99% by weight of peroxidized lipids and from 0.1% to 25% by weight of zinc oxide as a sole source of zinc, wherein said composition is non-aqueous.

2. A composition according to claim 1, wherein the peroxidized lipids present a peroxidation level lying in the range 5 to 600 milliequivalents per kg of peroxidized lipids.

3. A composition according to claim 1, wherein the peroxidized lipids present a peroxidation level lying in the range 30 to 500 milliequivalents per kg of peroxidized lipids.

4. A composition according to claim 1, wherein said peroxidized lipids comprise, as active agents, or as majority constituents relative to the total of active principles, partially oxidized triglycerides satisfying the formula:

in which R is partially peroxidized $C_{18}$ unsaturated acids.

5. A composition according to claim 1, wherein said peroxidized lipids are obtained by peroxidizing lipids or fats derived from natural vegetable oil.

6. A composition according to claim 5, wherein the natural vegetable oil is selected from the group consisting of sweet almond oil, hazelnut oil, peanut oil, corn oil, grapeseed oil, sesame oil, and safflower oil, and any mixtures thereof.

7. A composition according to claim 1, wherein the zinc oxide is in a micronized form.

8. A composition according to claim 1, in the form of an oily gel.

9. A composition according to claim 8, wherein said oily gel comprises said peroxidized lipids, said zinc oxide, a gelling agent, and optionally preservatives and/or fragrance or flavoring and/or formulation additives for improving the dosage form or for facilitating application of the composition.

10. A topical oily composition comprising, in percentages by weight: peroxidized lipids from 50% to 99%; and zinc oxide, as sole source of zinc, from 0.1% to about 1.0%, wherein said composition is non-aqueous.

11. The topical composition of claim 10, comprising, in percentages by weight: peroxidized lipids from 50% to 95%; zinc oxide, as sole source of zinc, from 0.1% to about 1.0%; a gelling agent, comprising silicon dioxide, from 1% to 10.0%; optionally, a preservative agent from 0.1% to 1.0%; and, optionally, flavoring from 0.5% to 5%.

12. A topical oily composition comprising, by weight: about 88% peroxidized corn oil, about 1% micronized zinc oxide as sole source of zinc, and about 7% silicon dioxide gelling agent, wherein said composition is non-aqueous.

13. A topical oily composition comprising, by weight: about 92% peroxidized corn oil, about 1% micronized zinc oxide as sole source of zinc, and about 7% silicon dioxide gelling agent, wherein said composition is non-aqueous.

14. A medical device comprising the topical composition of claim 1.

15. The medical device according to claim 14, wherein said medical device is for treating symptoms of herpes comprising pain, burning, itching, pricking, edema, ulceration/erosion, erythema, papules, vesicles, and crusts.

16. The medical device according to claim 14, wherein said device is for the treatment of symptoms of labial herpes.

17. The medical device according to claim 14, for the treatment of symptoms of genital herpes.

18. A medical device, comprising the topical composition of claim 10.

19. The medical device according to claim 18, wherein said medical device is for the treatment of symptoms of chronic itching sine materia, pricking, and scratching lesions.

20. A method of treating at least one body area in need thereof, selected from a skin area, an epidermis area, and a mucous membrane area, comprising a treatment selected from the group consisting of treating symptoms of burns, treating burns of post therapy or induced by pre-cancerous or cancerous treatments of skin, treating domestic burns, and burns induced by exposure to the sun, assisting healing or regeneration of skin or mucous membrane; acting on painful symptoms on the skin or the mucous membrane, comprising, applying topically on said body area, an effective amount, for treatment, of the oily composition according to claim 1.

21. The method of claim 20, wherein the treatment is selected from the group consisting of the treatment of symptoms of chronic itching sine materia, pricking, and scratching lesions.

22. A method of treating at least one body area in need thereof, selected from a skin area, an epidermis area, and a mucous membrane area, comprising, applying topically on said body area, the oily composition according to claim 1 in an effective amount for treating the symptoms of herpes selected from the group consisting of pain, burning, itching, pricking, edema, ulceration/erosion, erythema, papules, vesicles, and crusts.

23. A method of treating symptoms of labial herpes present on at least one body area in need thereof, selected from a skin area, an epidermis area, and a mucous membrane area, said method comprising, applying topically on said body area, a topical oily composition comprising, in percentages by weight: peroxidized lipids from 50% to 95%; zinc oxide, as sole source of zinc, from 0.1% to about 1.0%; a gelling agent, comprising silicon dioxide, from 1% to 10.0%; optionally, a preservative agent from 0.1% to 1.0%; and, optionally, flavoring from 0.5% to 5%; wherein said composition is non-aqueous.

24. A method of treating symptoms of genital herpes present on at least one body area in need thereof, selected from a skin area, an epidermis area, and a mucous membrane area, said method comprising, applying topically on said body area, a topical oily composition comprising, in percentages by weight: peroxidized lipids from 50% to 95%; zinc oxide, as sole source of zinc, from 0.1% to about 1.0%; a gelling agent, comprising silicon dioxide, from 1% to 10.0%;

optionally, a preservative agent from 0.1% to 1.0%; wherein said composition is non-aqueous.

25. The method of claim 24, comprising applying the composition three to five times per day on the area of the skin or the mucous membrane in need thereof.

\* \* \* \* \*